United States Patent
Schaefer et al.

[19]

[11] Patent Number: 5,908,379
[45] Date of Patent: Jun. 1, 1999

[54] URETHRAL CAP

[75] Inventors: Robert W. Schaefer, Bolton; Sergei Bogojavlensky, Harvard; Robert Schlesinger, Dedham, all of Mass.

[73] Assignees: Insight Medical Corporation, Bolton; NEBL, Inc., Worcester, both of Mass.

[21] Appl. No.: 08/914,970

[22] Filed: Aug. 20, 1997

Related U.S. Application Data

[63] Continuation of application No. 08/556,766, Nov. 2, 1995, abandoned, which is a continuation of application No. 08/476,092, Jun. 7, 1995, abandoned.

[51] Int. Cl.⁶ .................................................. A61F 2/00
[52] U.S. Cl. .................................... 600/29; 128/DIG. 25
[58] Field of Search ................ 600/29–32; 128/DIG. 25; 604/329–332, 337–338

[56] References Cited

U.S. PATENT DOCUMENTS

| | | |
|---|---|---|
| 3,340,876 | 9/1967 | Hill . |
| 3,349,768 | 10/1967 | Keane . |
| 3,512,185 | 5/1970 | Ellis . |
| 3,661,155 | 5/1972 | Lindan . |
| 3,683,914 | 8/1972 | Crowley . |
| 3,705,575 | 12/1972 | Edwards . |
| 3,776,235 | 12/1973 | Ratcliffe et al. . |
| 3,958,564 | 5/1976 | Langguth . |
| 4,194,508 | 3/1980 | Anderson . |
| 4,256,093 | 3/1981 | Helms et al. ........................ 128/1 R |
| 4,421,511 | 12/1983 | Steer et al. . |
| 4,484,917 | 11/1984 | Blackmon . |
| 4,496,355 | 1/1985 | Hall et al. . |
| 4,563,183 | 1/1986 | Barrodale et al. . |
| 4,690,677 | 9/1987 | Erb . |
| 4,795,449 | 1/1989 | Schneider et al. . |
| 4,822,347 | 4/1989 | MacDougall . |
| 4,846,819 | 7/1989 | Welch . |
| 4,889,532 | 12/1989 | Metz et al. . |
| 4,904,248 | 2/1990 | Vaillancourt . |
| 5,074,855 | 12/1991 | Rosenbluth et al. . |
| 5,090,424 | 2/1992 | Simon et al. ........................ 128/885 |
| 5,131,906 | 7/1992 | Chen ..................................... 600/29 |
| 5,195,997 | 3/1993 | Carns . |
| 5,263,947 | 11/1993 | Kay . |
| 5,336,208 | 8/1994 | Rosenbluth et al. . |

FOREIGN PATENT DOCUMENTS

| | | |
|---|---|---|
| 947602 | 5/1974 | Canada . |
| 1 223 353 | 4/1958 | France . |
| 2542995 | 9/1984 | France . |
| 2817571 | 10/1978 | Germany . |
| 3633824A1 | 4/1988 | Germany . |
| 1467144 | 3/1977 | United Kingdom . |
| 2193438 | 2/1988 | United Kingdom . |
| WO90/08561 | 8/1990 | WIPO . |

OTHER PUBLICATIONS

Neurology and Urodynamics, vol. 15, No. 1, 1996, pp. 381–382.

*Primary Examiner*—John P. Lacyk
*Attorney, Agent, or Firm*—Wolf, Greenfield & Sacks, P.C.; Fish & Richardson, P.C.

[57] ABSTRACT

A urethral cap is provided for alleviating urinary incontinence when attached to the body of the user. The cap has at least a partially deformable cap body with a hand gripping portion and a body contacting encircling surface. The body defines a chamber so as to allow for a vacuum seal when applied to the body so that there is an atmospheric air pressure seal between the urethral cap and the body to prevent urinary flow beyond the urethral cap.

21 Claims, 2 Drawing Sheets

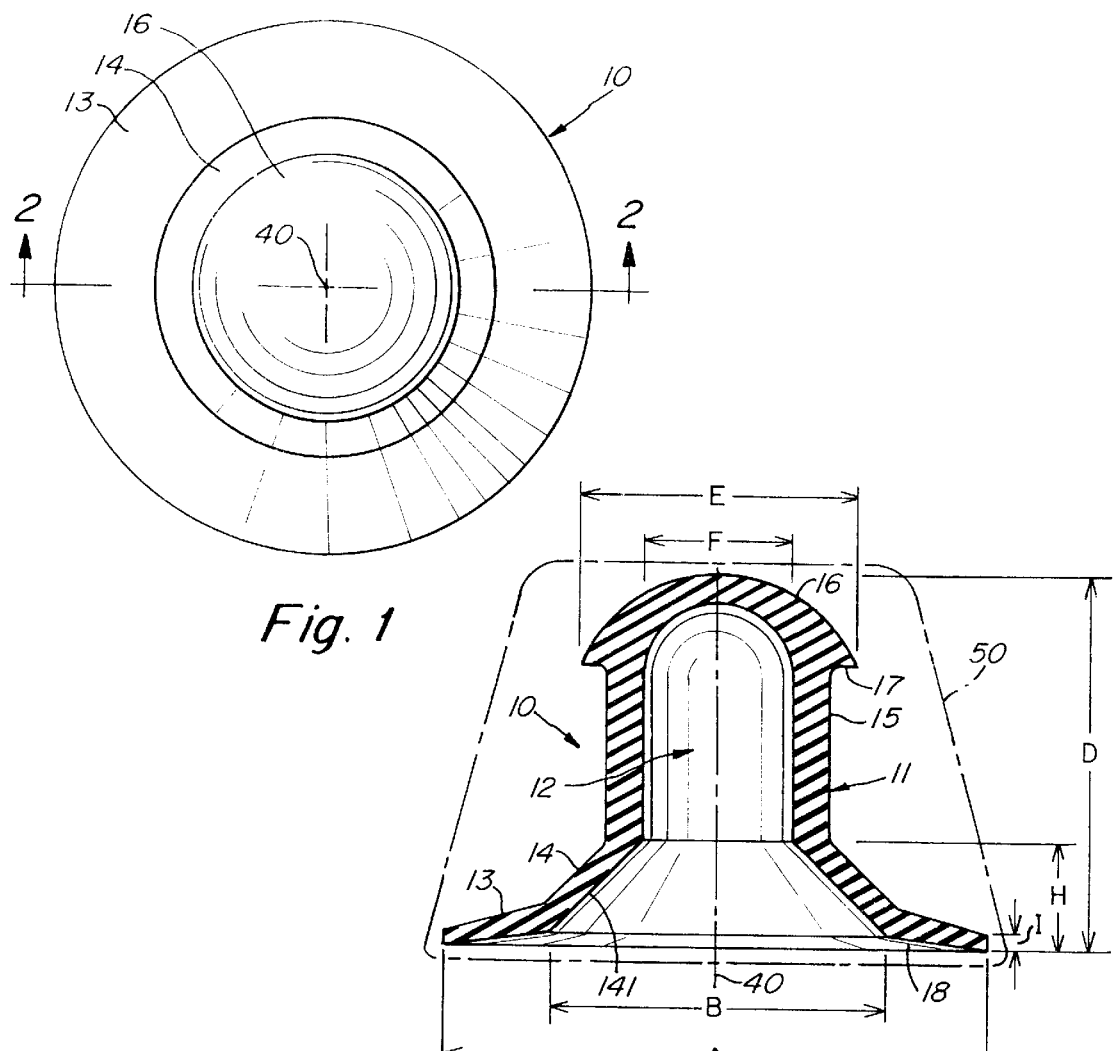
Fig. 1
Fig. 2
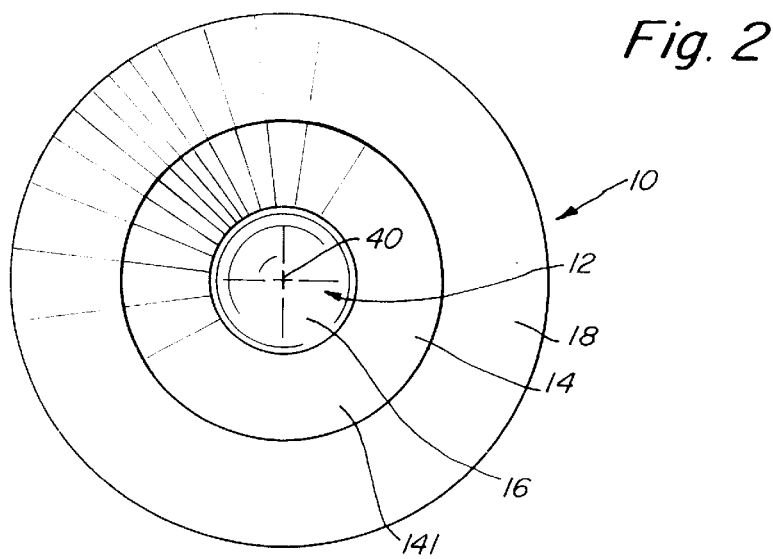
Fig. 3

URETHRAL CAP

This is a continuation of application Ser. No. 08/556,766, filed Nov. 2, 1995, now abandoned which is a continuation of U.S. application Ser. No. 08/476,092, filed Jun. 7, 1995, now abandoned incorporated herein by reference.

BACKGROUND OF THE INVENTION

Urinary incontinence, such as stress incontinence, in females is a substantial problem throughout the world. A variety of mechanisms have been suggested for use to alleviate the condition which can be a social as well as medical problem to those afflicted with the problem.

Many suggested medical devices to alleviate urinary incontinence in females require the use of internal components such as catheters, balloons, pessary or the like which pass into the urethra and are positioned within the body in use. Such internal components can be a source of irritation to the body and is in some cases can result in infection or other unwanted body reactions. Moreover, such devices as are known can be expensive and/or inconvenient to use and transport for use.

SUMMARY OF THE INVENTION

It is an object of this invention to provide a urethral cap for alleviating urinary incontinence such as stress incontinence in females which cap is inexpensive to provide, is simple to apply and remove and which does not create a high risk of body infection.

Still another object of this invention is to provide a urethral cap in accordance with the preceding cap which utilizes atmospheric pressure to maintain the cap in position on the body of a user.

Still another object of the present invention is to provide a urethral cap in accordance with the preceding objects which can incorporate a sealing material which can be a lubricant or adhesive to aid attachment to the body.

Still another object of the present invention is to provide a method of alleviating urinary incontinency in a user by applying a urethral cap blocking the outer orifice of the urethra at the meatus, and utilizing an air pressure difference to maintain the cap on the body of a user.

Still another object of this invention is to provide a method in accordance with the preceding method wherein an adhesive is used in conjunction with holding the cap on the body.

Still another object of this invention is to provide a method in accordance with the preceding objects which can be rapidly carried out by a user and provides safe and certain protection against incontinency in women.

According to the invention, a urethral cap for alleviating urinary incontinency when attached to the body of a user has a resilient at least partially deformable cap body with a hand gripping portion. The body defines a chamber sized to allow for reciprocal resilient deformation of the cap body to provide a vacuum therein to hold the urethral cap on the body of a user. A lower portion of the chamber acts to contact the meatus to constrict the meatus when the cap is applied to the body. The cap body further defines an encircling flange having a body contacting surface to act as a sealing surface with the body of a user.

Preferably, this encircling flange has a diameter of about 3 centimeters and preferably in the range of about 2.4 to 3.3 centimeters to allow proper positioning on the female body at the orifice of the urethra. Preferably, the cap is formed of a resilient body compatible rubbery material such as silicone rubber and can be sterilized and packaged under sterile conditions.

According to the method of this invention, urinary incontinence in women is alleviated and unwanted urinary flow prevented by applying a urethral cap having an internal chamber, over a urethra outer body orifice of the user. The cap defines a hand gripping portion and an encircling flange having a body contact surface which aids in sealing the urethral cap to the body of the user. Air pressure is employed below atmospheric air pressure to maintain the cap in place and compress the meatus. The urethral cap is removed to allow voiding when desired and can be reapplied.

It is a feature of this invention that the chance of infection and internal irritation to a user is reduced since no components of the cap pass into or through the urethra of the user and the cap is external to the body. The cap can be made of standard nonirritating body compatible materials such as silicone rubbers and the like. In use, the air pressure difference between the chamber of the cap and the atmosphere holds the cap in place. This positioning can be enhanced by use of an adhesive sealing material if desired, and/or is preferably enhanced by the use of a non-adhesive sealing material. The sealing material can be preapplied. The cap allows for collection of a small amount of urine in an internal chamber as well as ease of removal to allow urinary flow and ease of replacement. In ordinary use, the meatus is closed by the urethral cap and no urine leakage occurs to the chamber or outside of the body. The cap can be made relatively inexpensively of inexpensive materials in proper sizing as required. A small number of sizes can be used to fit the vast majority of users.

BRIEF DESCRIPTION OF THE DRAWINGS

The above and other objects, features and advantages of the present invention will be better understood from the following description when read in conjunction with the accompanying drawings, in which:

FIG. 1 is a top view of a preferred embodiment of the urethral cap in accordance with this invention;

FIG. 2 is a cross-sectional view thereof taken through line 2—2 of FIG. 1;

FIG. 3 is a bottom view thereof;

DETAILED DESCRIPTION

Figure 4:
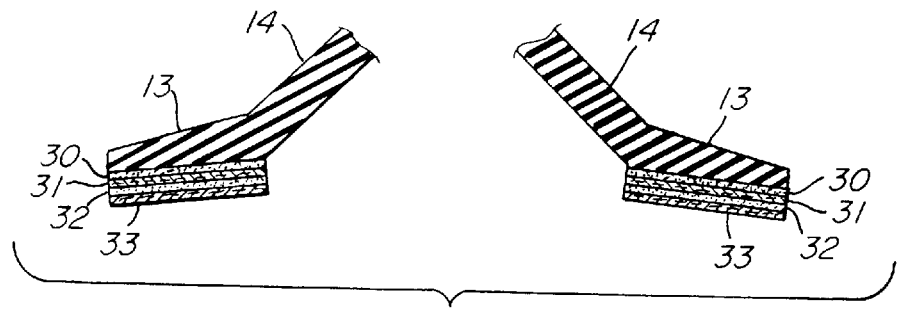
FIG. 4 is a cross-sectional view through a section of the flange of a cap in accordance with FIG. 1 having a plurality of sealing layers applied thereto.

A preferred embodiment of a urethral cap or incontinence device is illustrated at 10 as best shown in FIGS. 1–3. The cap comprises a body 11 defining an inner chamber 12 with an outer flange 13 and an intermediate frustoconical portion 14.

The body of the urethral cap in the preferred embodiment of FIG. 1 has a cylindrical wall 15 around a central axis 40 of the cap, with a rounded outer end wall 16, a finger gripping ledge 17 and a body contacting encircling surface 18 are provided.

The urethral cap is preferably integrally formed as by conventional molding but can be made by dipping, spraying or other techniques. The material of the integral cap is preferably an FDA approved medical grade silicone rubber. However, elastomeric materials such as medical grade silicone rubber sold by Dow Corning Co., elastomeric urethanes, polyvinyl chlorides, natural and other rubbery material or synthetic polymeric materials can be used. In some cases, the body need not be integrally formed but can be formed of rigid materials which can be polymeric or metallic. In these cases, at least a portion of the body opening into the interior chamber 12 is formed of a resilient material which can be elastically and reciprocally moved by the fingers from the at rest position as shown in FIG. 2 to a compressed or reduced chamber position and then allowed to expand to the at rest position. This is necessary in order to provide at least a partial vacuum in the chamber to seal the cap to the body by an air pressure differential between the air within the chamber and the atmospheric air pressure as will be described.

The side wall thickness of the cap is arranged so that side wall 15 has a thicker section and is more resistant to collapse or deformation by atmospheric pressure than is the flange portion 13 which tapers from the wall 15. The thickness of wall 15 can be, for example, 1.75 millimeter thick with a preferred range of 1.5 to 2.5 millimeter, with a flange 13 thickness I of, for example, 0.75 millimeter in the preferred embodiment and a preferred range of 0.5 to 1.5 millimeter and can be formed of an FDA approved medical grade silicone rubber. This difference in wall thickness prevents collapse on itself of the device in use, yet, allows for movement of the flange towards the body in use.

Figure 6:
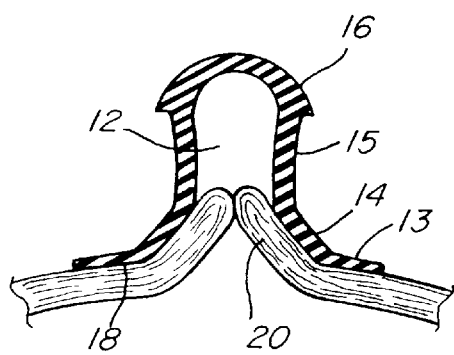
FIG. 6 is a diagrammatic cross-sectional view as through line 2—2 of FIG. 1 of the urethral cap when in place on the body of the user.

As best seen in the cross section of FIG. 6, the flange 13 can be deformed towards or closely contact the body at the planar area of the body surrounding the meatus or urethra orifice. A portion of orifice of the urethra indicated at 20 can be drawn into contact with the flange 13 and the frustoconical portion 14 which acts to close the meatus in order to maintain position of the cap, to form a good seal with the body at flange 13 and to close the meatus to urine flow.

In use, the meatus is preferably closed by a gentle compression of the area around the meatus to form a closure maintained in position by an air pressure difference. Any structure that provides a closure of the meatus to urine flow, yet allows comfort in use and ease of reuse, can provide the advantages of this invention. These advantages can be obtained by the device 10 acting solely externally of the body without any part thereof entering the body of a user.

The end wall 16 of the cap preferably provides a hand gripping wall 17 although any configuration which allows for finger gripping of the cap to allow positioning on the body and removal therefrom by the fingers of the user is acceptable. Thus, although the cap is shown as a cylindrical side wall, rounded end wall top with frustoconical section 14 and encircling flange 13, the shape can vary greatly. The section 14 is important to provide the closure of the meatus. Generally, the angle of the interim wall surface 141 with the surface 18 is obtuse to enhance closure of the meatus. This internal wall surface 141 is a lower portion of chamber 12 and closes the meatus by pressure thereof.

It is preferred that the flange 13 provide a body contacting surface 18 forming a continuous ring about the opening or meatus of the urethra of the body. However, other portions of the cap can be square, round, oblong, bulbous, or of any shape desired. Flat, rather than rounded end wall 16 can be used. In all cases, sufficient interior space is provided at the inner chamber 12 which extends to the tip of the flange, to provide for forming an at least partial vacuum in the chamber by finger compression, and allowing resilient rebound to the positioning as in FIG. 6.

The dimensions of the urethral cap can vary greatly. However, consistent with normal anatomy of females in the United States, it is preferred that the diameter A be in the range of 2.3 to 3.4 centimeters and more preferably 2.4 to 3.3 centimeters with 3 centimeters being used in the preferred embodiment. Where the flange 13 is oval or of other encircling shapes such as square, oblong, triangular or the like, the maximum flange width corresponding to the diameter of flange 13 between the labia is about 3.4 centimeters. Diameter B is preferably in the range of 1 centimeter to 2.5 centimeters with 1.5 millimeters being preferred. The height D of the device is preferably 1 to 3 centimeters and in the preferred embodiment 2 centimeters. This height can vary greatly but by maintaining the device approximately 1 to 3 centimeters in height, the device can be worn without discomfort, positioned easily and is resistant to dislodging by garments worn by the user.

Distance E can be, for example, 1.35 centimeters in the preferred embodiment with the chamber diameter of chamber 12 shown at F being 75 millimeters in the preferred embodiment. Distance H which defines in part the interior chamber can be 5.25 millimeters in the preferred embodiment but again can vary greatly. The most important dimensions relate to the range of 2.3 to 3.4 centimeters in outer diameter of flange 13 for proper positioning in the body and preferably the height is no more than about 3 centimeters to allow ease of use and reuse.

In the preferred embodiment, Silastic HS-30, manufactured by Dow-Corning Corp. of Midland, Mich., is used as the elastomeric material for the integral cap 10. The Silastic HS-30 preferably has a Durometer Shore A of 32, tensile strength psi (Mpa) 1325(9.13) and an elongation of 1020%. The Silastic silicone rubber can be cured with conventional peroxide curing agents such as Lupersol 101, a product of Penwalt Corp. of Buffalo, N.Y. Conventional colorants can be used to add color as, for example, organic and inorganic pigments.

In use, a sealant material which can be an adhesive but need not be an adhesive, is applied to the body contacting surface 18. The purpose of this material shown in FIG. 4 at 30 is to provide an air and liquid seal between the skin of the body and the flange. If the seal is adhesive, it not only seals against air and liquid pressure leakage, but can also act to hold the device in contact with the body. However, it is preferred not to use solely an adhesive as the body adhering portion since this could be irritating to the body if sufficient adhesive is used to provide proper protection. On the other hand, when substantially no adhesive properties are used in the sealing material, sufficient protection against urinary leakage is provided by the incontinence device 10 of this invention.

The cap preferably is symmetrical about a central axis 40 shown in FIGS. 2 and 3 although it need not be symmetrical in all embodiments.

The sealing material 30 can be known adhesives which are nonirritating to the body and can be used in contact with the body over a period of time. Such adhesives include the water soluble paste FIXADENT® or CONFIDENT an adhesive produced by Block Drug of Jersey City, N.J. However, sealing materials such as conventional lubricants including petrolatum or petroleum jelly such as Vaseline® can be used without adhesive properties. The sealing material such as petroleum jelly compensates for irregularities in the skin or cap sealing surface flange and thus provides for protection against air and urine leakage in use of the device when the device is applied to the body.

The sealing material 30 can be applied by the user using a Q-tip applicator or the fingertip to rub the vaseline or adhesive over the body sealing surface just prior to use. In some cases, the lubricant or adhesive can be prepositioned on the device with a cover or release strip 31 applied thereover to prevent sticking or removal of the sealant or adhesive prior to application. In some cases, a plurality of sealant and cover strips can be used as suggested in FIG. 4 at 32 and 33. Thus, in the first application, the lower strip 33 is removed exposing an underlying surface 32 of adhesive or lubricant sealing material for a first application to the body. This can be done where the sealant directly contacting the flange directly is an adhesive and, thus, the product is maintained on the body. After first removal, the second cover strip 31 can be removed to expose the underlying adhesive 30 for a second application. Any number of protective strips and sealant layers can be used as desired. In the preferred embodiment, the sealant material is applied just prior to use by the user as when vaseline petroleum jelly is used.

Figure 5:
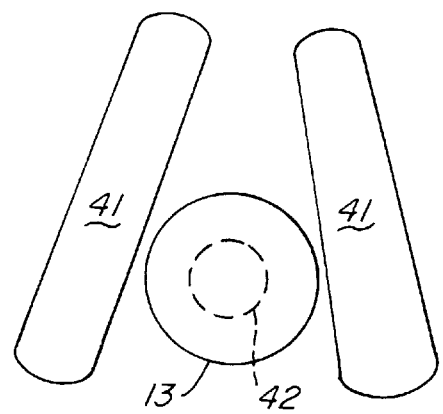
FIG. 5 is a semi-diagrammatic top plan view of the urethral cap of FIG. 1 in place on the body of the user.

FIGS. 5 and 6 diagrammatically show placement on the body. In FIG. 5, the labia 41 are diagrammatically illustrated with the urethral opening or meatus 42 being shown with the flange 13 positioned thereover. In FIG. 6, the cap 10 is shown in position with the skin of the body about the meatus pulled into direct contact with the body contacting surface 18 of the flange and the underside of the frustoconical portion 14. This closes the urethral orifice and the positioning of the skin below the flange acts to aid in centering and maintaining the cap in position on the body as well as to prevent urine outflow. Similarly, because the flange 13 is positioned to lie substantially just within the labia 41 at a planar area around the meatus, positioning is maintained and this spacing aids in locating and placing the urethral cap in position.

In the method of applying the urethral cap of this invention, the cap is deformed inwardly by the fingers of the user and then applied to the orifice of the urethra and allowed to expand to its original shape as shown in FIG. 2. This creates a vacuum within the inner chamber 12 causing outside atmospheric pressure to push against the flange 13 and frustoconical portion 14 and maintain the urethral cap in good sealing engagement with the body. The skin or tissue immediately surrounding the meatus is compressed by the air pressure difference and a seal is formed with the cap 10 at the surface 141. The sealing material preapplied to the body contacting surface 18 aids in maintaining the seal. The pressure differential between the inside of the cap and the atmosphere can vary greatly. This depends in part on atmospheric conditions as well as how much depression is applied to the chamber before it resiliently returns to its normal position shown in FIG. 2. In some cases, the full repositioning of FIG. 2 is not achieved after compression of the side wall in application, but in all cases, some chamber vacuum or partial vacuum remains inside the cap. The interior chamber 12 can act as a reservoir if there is some leakage while the cap is in place, although this does not normally occur.

As previously noted, the skirt size is such that it aids in positioning the skirt in proper position over the urethral orifice and also maintaining the cap in place. The finger grip is important for placement particularly in older patients. The finger grip can be simply the cylindrical outer surface of chamber 12.

The differential in air pressure between the inside of the cap and the atmosphere is difficult to determine. In many cases, the air pressure differential may be as little as 1 psi or can be 2–5 psi or 6–10 psi or more. Preferably, the pressure is applied by the depression of the cap and the expansion thereof towards its original shape since the walls are resiliently deformable. This can result in different amounts of pressure when even the same cap is used depending on how it is applied and how much depression occurs. Surprisingly, it has been found that even with small caps following the method of this invention, sufficient air pressure difference is obtained to maintain the cap in position and avoid urine flow.

Thus, a user can alleviate urinary incontinence such as stress incontinence by applying the cap over the urethral orifice using the labia spacing to help position the cap. Prior to contact with the body, the cap is resiliently depressed at the hand gripping portion and the encircling flange is brought into contact with the skin surrounding the orifice opening. The body contacting portion of the flange has been previously treated with petroleum jelly or an adhesive as previously described. Slight pressure on the skin and release of the pressure deforming the cap causes a suction within the cap and provides the air pressure difference on the outside of the flange and frustoconical portion 14 that maintains the cap in place on the body and closes the meatus as shown in FIG. 6. The cap can be easily removed to allow voiding when desired. In some cases, the cap can merely be pulled off the skin although a slight depression of the finger gripping portion is desired to alleviate the pressure difference first. The device is comfortable in use, can be easily applied by a majority of patients and has been found to prevent urinary leakage and thus alleviate urinary incontinence in women, including stress urinary incontinence.

In the preferred embodiment, the cap is packaged in a surrounding clear plastic container or envelope diagrammatically illustrated at 50. This maintains the cleanliness of the cap prior to usage. Such envelopes are known in the art and can comprise thin plastic films which can be see through or opaque. Other conventional packages can be used to store and transport the urethral cap to maintain cleanliness. In some cases, a plurality of caps can be packaged in a single package or no package need be used. In some cases, the caps of this invention can be sterilized. Preferably, the caps 10 of this invention are manufactured and packaged under and meeting ISO 9000 standards to provide cleanliness, manufacturing quality and lot control. Thus, contamination, including bacterial contamination, is minimized.

The urinary caps of this invention can be sterilized to reduce the risk of infection or irritation to the skin. Sterilization is not required since the device is external to the body and does not have any component passing within the urethra.

It has been found that caps of this type are useful for long periods of time and maintain the contact with the skin in sealing arrangement for periods of 2 to 6 hours or more in some cases.

While specific embodiments of this invention have been shown and described, it will be obvious to those skilled in the art that many variations are possible. The particular materials, integral nature, geometric configuration of the devices of this invention can vary greatly. In all cases, a pressure differential is instrumental in providing a body contacting seal to alleviate conditions of incontinency which seal acts along with a mechanical closure of the meatus. The seal formed by the flange 13, portion 14 and the body by the air pressure difference between the chamber and atmosphere and the adhesive contact if used, is sufficiently strong to withstand and to prevent urinary flow out of the cap over long periods of time at urinary pressures normally encountered at the urethral orifice.

What is claimed is:

1. A urethral cap adapted to be applied over the meatus of the body of a user for alleviating urinary incontinence, said cap comprising a resilient at least partially deformable cap body having a hand gripping portion, said body defining a chamber there within sized to allow for reciprocal resilient deformation of said cap body to provide a vacuum therein adapted to hold said urethral cap on the body of a user and close the meatus of said body of the user, said cap body defining an encircling flange having a cap body contacting surface adapted to act as a sealing surface with the body of a user.

2. A urethral cap in accordance with claim 1 and further comprising a sealing material covering said cap body contacting surface adapted to aid in preventing fluid flow between said cap body contacting surface and the body of an individual when said cap is in use.

3. A urethral cap in accordance with claim 1 wherein said encircling flange has an outer diameter of from about 2.3 to about 3.4 centimeters.

4. A urethral cap in accordance with claim 2 wherein said encircling flange has an outer diameter of about 3 centimeters.

5. A urethral cap in accordance with claim 1 wherein said chamber defines a central axis passing from a top of said cap to a bottom of said cap, with said bottom being defined by said encircling flange, said top to bottom having a height of about 2 centimeters.

6. A urethral cap in accordance with claim 1 wherein said cap is integrally formed of a resilient material which allows ease of application to the body of a user by deforming said cap chamber, applying said cap to the user body about the orifice of a urethra and releasing said deforming pressure to define an air pressure difference between said chamber and the atmosphere sufficient to seal said flange to the user and to prevent liquid flow there through at normal pressures encountered in urinary fluids expressed by the body, said cap further defining a meatus constricting surface portion to close said meatus when said cap is applied with said pressure difference acting to position said cap.

7. A urinary cap in accordance with claim 1 wherein said cap is formed of an FDA approved silicone rubber.

8. A urinary cap in accordance with claim 1 carrying a layer of the sealing material over said body contacting surface, and a release strip covering said sealing material.

9. A urethral cap in accordance with claim 8 and further comprising a second layer of sealing material over said release strip and a second release strip overlying said second layer of sealing material.

10. A urethral cap in accordance with claim 2 wherein said sealing material is a lubricant with no adhesive properties.

11. A urethral cap in accordance with claim 2 wherein said sealing material is an adhesive.

12. A urethral cap in accordance with claim 2 wherein said cap is integrally formed of a silicone rubber material compatible with and nonirritating to the skin of the body.

13. A urethral cap in accordance with claim 2 wherein said encircling flange has an outer diameter of from about 2.3 to about 3.4 centimeters.

14. A urethral cap in accordance with claim 5 and further comprising a sealing material covering said body contacting surface for aiding in preventing liquid flow between the body contacting surface and the body of an individual when said cap is in use.

15. A urethral cap in accordance with claim 14, wherein said cap provides a generally frustoconical inner surface adjacent to said flange body contacting surface adapted to aid in closing said meatus by compression when said cap is in use.

16. A method for alleviating urinary incontinence of a user, said method comprising:

applying a urethral cap having an internal chamber over a urethra outer body orifice of a user, said cap defining a hand gripping portion and an encircling flange having a body contacting surface area which aids in sealing said urethral cap to the body of a user, employing air pressure within said cap below ambient atmospheric air pressure to maintain said cap in place, and removing said urethral cap to allow voiding when desired.

17. A method in accordance with the method of claim 16 wherein a sealing material is applied to said body contacting surface before application of said cap to the body orifice of a user, and said air pressure acts to compress and seal the meatus to urinary flow.

18. A method in accordance with the method of claim 17 wherein said urethral cap is applied by resiliently compressing said cap, contacting said body contacting surface area with the body of the user, positioning a central axis of said cap over said urethra outer body orifice, and allowing said cap to resiliently return towards its original configuration.

19. In a method of preventing unwanted urinary flow from the body of a female user, the method comprising:

applying a urethral cap over the orifice of the urethra and maintaining said cap in place on the body of the user by the use of reduced air pressure within said cap to prevent urinary flow beyond said cap.

20. In a method of alleviation of urinary incontinence, wherein a hand applied device is used to prevent unwanted urinary flow, the improvement comprising, using a hand applied and removable device mounted externally of the body to close the meatus of the body to urinary flow, positioning said device over the meatus of the body of a user and maintaining it in place by the use of an air pressure differential, and removing said device from the body to allow the meatus to return to its opened natural state and permit urinary flow when desired.

21. A urethral cap adapted to be attached to the body of a user for alleviating urinary incontinence, while minimizing infection of the user by avoiding the use of components of said cap passing into or through the urethra of a user, said cap having an interior surface and an exterior surface and defining an interior chamber for establishing a pressure differential between said urethral cap and the atmosphere and adapted to aid in maintaining said cap in position attached to said body, said cap comprising a hand gripping portion for use in mounting said cap over the urethra external orifice of said body, a meatus compressing and closure surface portion, and an encircling flange having a body contacting surface adapted to act as a sealing surface with the body of a user, said encircling flange being constructed and arranged to surround said urethra external orifice.

* * * * *